United States Patent
Donath

(10) Patent No.: US 7,585,315 B2
(45) Date of Patent: Sep. 8, 2009

(54) DEVICE FOR CONNECTING A LONGITUDINAL MEMBER TO A BONE

(75) Inventor: Raoul Donath, Grenzach-Wyhlen (DE)

(73) Assignee: Synthes USA, LLC, West Chester, PA (US)

( * ) Notice: Subject to any disclaimer, the term of this patent is extended or adjusted under 35 U.S.C. 154(b) by 950 days.

(21) Appl. No.: 10/916,570

(22) Filed: Aug. 10, 2004

(65) Prior Publication Data

US 2005/0080419 A1   Apr. 14, 2005

Related U.S. Application Data

(63) Continuation of application No. PCT/CH02/00080, filed on Feb. 11, 2002.

(51) Int. Cl.
   *A61B 17/70* (2006.01)
(52) U.S. Cl. .................. 606/269; 606/272; 606/278
(58) Field of Classification Search .................. 606/61, 606/265, 267, 269, 272, 277; 403/290, 344, 403/370, 371, 398, 399; 411/400, 410; 384/903; 24/19, 268, 537, 542; 248/64, 71, 74.1–74.5
See application file for complete search history.

(56) References Cited

U.S. PATENT DOCUMENTS

| | | | | |
|---|---|---|---|---|
| 124,071 A | * | 2/1872 | Lipsey | 24/537 |
| 134,756 A | * | 1/1873 | Marston | 40/664 |
| 612,685 A | * | 10/1898 | Thorp et al. | 403/290 |
| 1,110,579 A | * | 9/1914 | Seeber | 24/537 |
| 1,182,288 A | * | 5/1916 | Mack | 403/370 |
| 1,194,509 A | * | 8/1916 | Kosovsky | 24/535 |
| 1,301,885 A | * | 4/1919 | Tobiason et al. | 24/537 |
| 4,987,892 A | * | 1/1991 | Krag et al. | 606/61 |
| 5,584,834 A | | 12/1996 | Ralph et al. | |
| 5,607,426 A | * | 3/1997 | Ralph et al. | 606/61 |
| 5,683,392 A | * | 11/1997 | Richelsoph et al. | 606/61 |
| 5,728,098 A | | 3/1998 | Sherman et al. | |
| 5,989,250 A | * | 11/1999 | Wagner et al. | 606/61 |
| 5,997,539 A | * | 12/1999 | Errico et al. | 606/61 |
| 6,171,311 B1 | * | 1/2001 | Richelsoph | 606/61 |
| 6,254,602 B1 | | 7/2001 | Justis | |
| 6,273,888 B1 | | 8/2001 | Justis | |
| 6,299,614 B1 | * | 10/2001 | Kretschmer et al. | 606/61 |
| 6,328,741 B1 | * | 12/2001 | Richelsoph | 606/61 |
| 7,090,674 B2 | * | 8/2006 | Doubler et al. | 606/61 |
| 2001/0012937 A1 | * | 8/2001 | Schaffler-Wachter et al. | 606/61 |
| 2002/0159828 A1 | * | 10/2002 | Rotshtain | 403/371 |

* cited by examiner

*Primary Examiner*—Thomas C Barrett
*Assistant Examiner*—Jay R Sigler
(74) *Attorney, Agent, or Firm*—Stroock & Stroock & Lavan LLP

(57) ABSTRACT

The present invention is directed to a device for connecting a longitudinal member to a bone, the device including a lower part for fixation to the bone and an upper part having a transverse channel for receiving the longitudinal member and a slit defining a pair of elastically displaceable sidewalls. The device further includes a locking ring. The locking ring is moveable from a first position, wherein the sidewalls are elastically displaceable so that the longitudinal member can be moved into the channel, to a second position, wherein the sidewalls are substantially fixed with respect to each other so that the longitudinal member placed within the channel is fixed with respect thereto. The device further including a first groove sized and configured to receive the locking ring when in the first position and a second groove sized and configured to receive the locking ring when in the second position.

30 Claims, 4 Drawing Sheets

DEVICE FOR CONNECTING A LONGITUDINAL MEMBER TO A BONE

CROSS-REFERENCE TO RELATED APPLICATION

This application is a continuation of International Patent Application No. PCT/CH02/00080 filed on Feb. 11, 2002.

TECHNICAL FIELD

The invention relates to a device for connecting a longitudinal member to a bone.

BACKGROUND OF THE INVENTION

For the internal fixation of the spinal column or portions thereof, preferably devices are used, which include pedicle screws, at least one longitudinal member, and connecting members for connecting the pedicle screws to the longitudinal member. The pedicle screws are screwed into the pedicle of the vertebra bodies, which are to be connected and fastened with their screw heads in the connecting member. In order to anchor the implant, the pedicle screws, on the one hand, must be anchored firmly in the pedicles of the vertebra bodies and, on the other, must be rigidly connect with the longitudinal member. The screw head and the connecting member may be connected by a clamping mechanism, which may be disconnectable, so that the implant may be removed without having to produce large openings in the tissue in the region of the spinal column.

A device for connecting a pedicle screw with a longitudinal member is disclosed in U.S. Pat. No. 5,728,098 to Sherman et al. This known device includes a pedicle screw with a spherical screw head and a connecting member having a cavity, which, towards the lower end adjoining the pedicle screw, is also constructed spherically to accommodate the screw head of the pedicle screw. At the upper end of the connecting member, a channel for accommodating a longitudinal member is disposed transversely to the longitudinal axis of the connecting member. Two sidewalls, forming the boundary of the channel, as well as the lower segment of the connecting member are elastically deformable transversely to the longitudinal axis. This enables, on the one hand, after the head of the pedicle screw is inserted, the lower segment of the connecting member to be compressed transversely to the longitudinal axis and, as a result, the screw head may be fixed in the cavity and, on the other hand, after the longitudinal member is placed in the channel, the upper segment of the connecting member may be compressed transversely to the longitudinal axis, so that the longitudinal member may be fixed in the channel between the sidewalls. The upper and lower ends of the connecting member are compressed by means of locking rings, which, for axial fixation, can be locked in position in grooves formed on the connecting member. It is a disadvantage of this device, however, that the locking ring, which fixes the longitudinal member in the upper segment of the connecting member, must be brought separately by the surgeon as an individual part to the implant after the longitudinal member is introduced into the channel, so that an additional step in the procedure is required. Moreover, bringing the locking ring over as a separate part increases the risk that the locking ring may be lost in the patient's body during implantation.

SUMMARY

It is an object of the present invention to resolve the deficiency of the prior art. That is, it is an object of the present invention to provide a device, the locking ring of which may be connected with the device before implantation and, after the longitudinal member is introduced into the channel formed in the upper part of the bone fixation means, the device may be locked simply by shifting the locking ring from a first position to a second position.

Pursuant to the invention, this objective is accomplished by a device for connecting a longitudinal member with a bone or bone fragment, the device having a bone fixation means with a central longitudinal axis, a coaxially disposed lower part for fixation with a bone and a coaxially disposed upper part having an upper end and a lower end, the upper part including a channel having an opening at the upper end with a channel axis directed transversely to the longitudinal axis for accommodating a longitudinal member; the upper part including a slit, between the lower end of the upper part and the channel, which extends parallel to the longitudinal axis and which passes radially through the upper part so that two sidewalls are formed and so that they may be deformed elastically and transversely with respect to the channel axis. The device further including a locking ring having a central borehole with a diameter d, the locking ring being displaceable to a second position, in which the two sidewalls are pressed against the channel axis so that the longitudinal member placed within the channel may be fixed in the device, characterized in that the upper part, between the lower end of the upper part and the channel, includes a first groove, which is concentric with the longitudinal axis and which has a core diameter $D_{K1}$, the core diameter $D_{K1}$ of the first groove being smaller than the diameter d of the central borehole formed in the locking ring, so that the locking ring may be shifted from a first position, in which the two sidewalls may be spread elastically with respect to the longitudinal axis; and the upper part, between the first groove and the channel, including a circular shoulder, concentric with the longitudinal axis, and which has an external diameter $D_A$, with diameter $D_A$ being greater than the diameter d of the central borehole formed in the locking ring.

That is, the inventive device may include a bone fixation means with an upper part for connection with a longitudinal member and a lower part for fixation with a bone, especially a pedicle of a vertebra. The longitudinal member may be inserted into a channel formed in the upper part, which has a channel axis extending transversely to the central longitudinal axis of the bone fixation means. The inventive device further includes a locking ring having a central borehole that extends coaxially with the longitudinal axis and, which may be moved from a first axial position, wherein the longitudinal member may be inserted into the channel, to a second axial position wherein the longitudinal member, once inserted into the channel, may be blocked relative to the bone fixation means, i.e., locked within the channel.

The inventive device may also include at least one slit, disposed parallel to the longitudinal axis between the lower end of the upper part and the channel so that the upper part may be elastically deformable transversely to the longitudinal axis. At least two sidewalls are formed in the upper part, by the channel and the at least one slit. The sidewalls may be deformed elastically transversely to the axis of the channel. Furthermore, the upper part may include a first circular groove, which is concentric with the longitudinal axis and which has a core diameter, which is smaller than the diameter of the central borehole formed in the locking ring, so that, in the first position, the locking ring axially coinciding with the first groove, the two sidewalls formed in the upper part of the bone fixation means may be deformed elastically transversely to the longitudinal axis and may also be deformed elastically transversely to the channel axis to enable the longitudinal member to be moved into the channel and, also, after the longitudinal member has been moved into the channel, to permit resetting maneuvers to be carried out on the bone, which is to be stabilized, for example, at the vertebra parts, which are to be stabilized.

During the resetting of the bones, which are to be stabilized, the longitudinal member may be locked in position by the two, elastically deformable sidewalls, so that the longitudinal member may be displaced or rotated in the channel against a slight resistance.

Therein the present invention permits: the pre-assembled implant to be implanted without running the risk of losing individual parts while still permitting the resetting of the bones.

In one preferred embodiment of the inventive device, the device may include an upper part, which, between the first groove and the lower end of the upper part, has a diameter D, which is larger than or equal to the diameter d of the central borehole formed in the locking ring. The ratio between the diameter D and the diameter d may preferably be between about 102% and about 100% and more preferably between about 100.5% and about 100%. With that, the advantage may be achieved that the locking ring, if the implant is preassembled, can be pushed or pressed over the upper part from the lower end of the bone fixation means up to the first groove. However, the locking ring cannot be shifted automatically out of the groove and over the lower end of the upper part. This property can be reinforced by designing the central borehole in the locking ring with a conical or spherical expansion at the upper end of the central borehole and with a sharp edge at the lower end of the central borehole.

In an alternate embodiment of the inventive device, the device may include a circular shoulder, which is concentric with the longitudinal axis, between the channel and the first groove. The ratio of the diameter of the shoulder $D_A$ to the diameter d of the central borehole formed in the locking ring is preferably between about 101% and about 110% and more preferably between about 101% and about 105%. With that, the advantage may be achieved that, after fixation of the longitudinal member in the channel, the locking ring cannot shift automatically axially over the groove and that the blocking of the device could be counteracted.

In an another embodiment of the inventive device, the device may also include, between the shoulder and the channel, a second groove, in which the locking ring may be locked in place for locking the longitudinal member placed in the channel. The ratio of the core diameter $D_{K2}$ of the second groove to the diameter d of the central borehole formed in the locking ring is preferably between about 102% and about 100% and more preferably between about 100.5% and about 100%. With that, the advantage may be achieved that the locking ring can be arrested axially in the second groove in the second position of the locking ring.

Preferably, the lower part of the bone fixation means is equipped as a pedicle screw having a screw shaft with an external thread. In other embodiments, the lower segment of the bone fixation means may be constructed as a pedicle hook.

Aside from the bone fixation means, the inventive implant may also include a rod-shaped longitudinal member having an external diameter $D_L$. Moreover, the channel formed in the upper part for receiving the longitudinal member may have an inside width $L_W$, the ratio of $L_W$ to $D_L$ preferably being between about 98% and about 102%. With that, the advantage can be attained that the longitudinal member is arrested elastically by the sidewalls formed on the upper part of the bone fixation means, when the longitudinal member is not in the blocked state, i.e., the second position, of the device. Consequently, resetting maneuvers may be carried out on the bone parts, especially at the spinal column parts, and the longitudinal member may nevertheless easily be tightly clamped.

Further advantageous developments of the invention are characterized in the dependent claims.

BRIEF DESCRIPTION OF THE DRAWINGS

The invention and further developments of the invention are explained in even greater detail in the following by means of partially diagrammatic representations of several examples. In the drawing.

DETAILED DESCRIPTION

Figure 1:
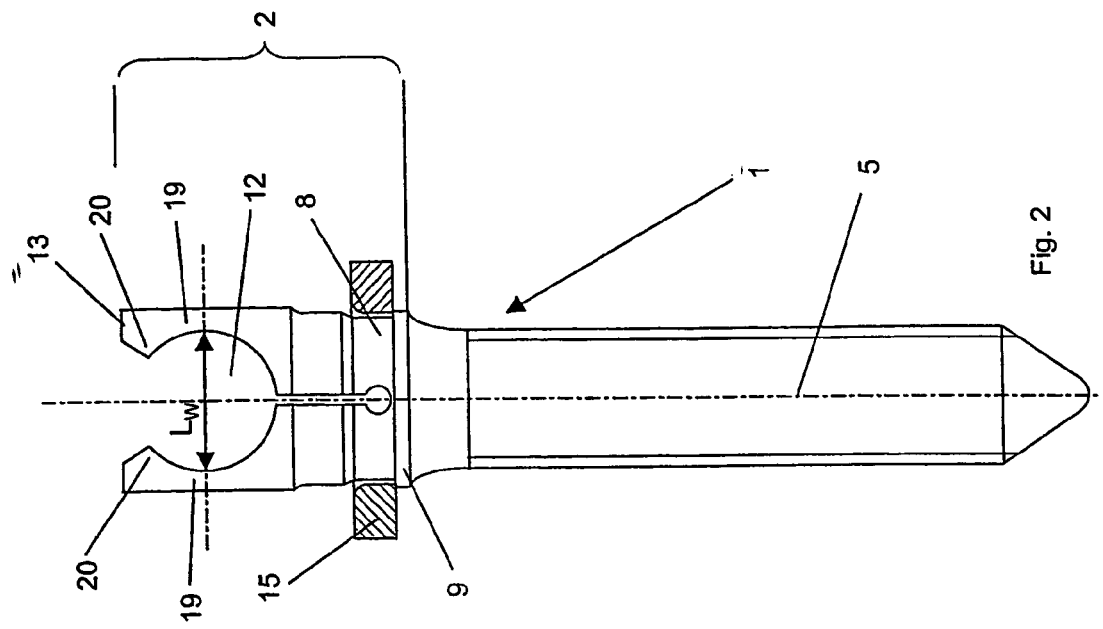
FIG. 1 shows a view of an embodiment of the inventive device with a blocked longitudinal member, i.e., with the locking ring in the second position.
Figure 2:
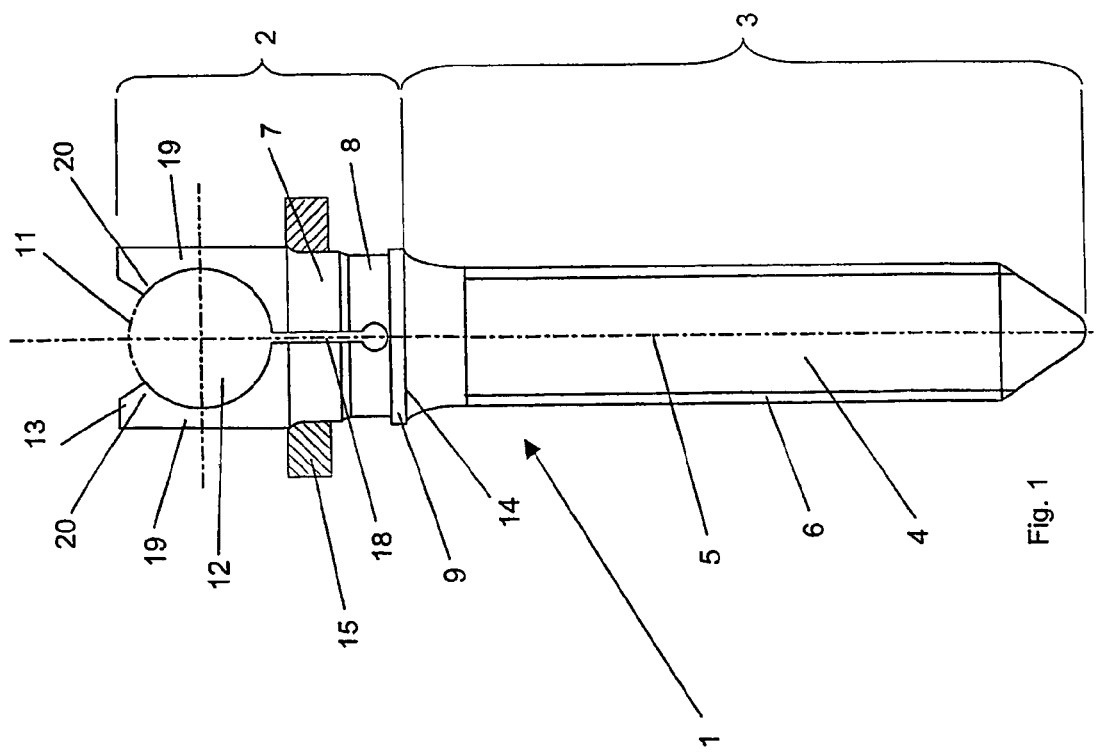
FIG. 2 shows a view of the embodiment of the inventive device, shown in FIG. 1, the locking ring being in the first position intended for resetting the bone parts.
Figure 3:
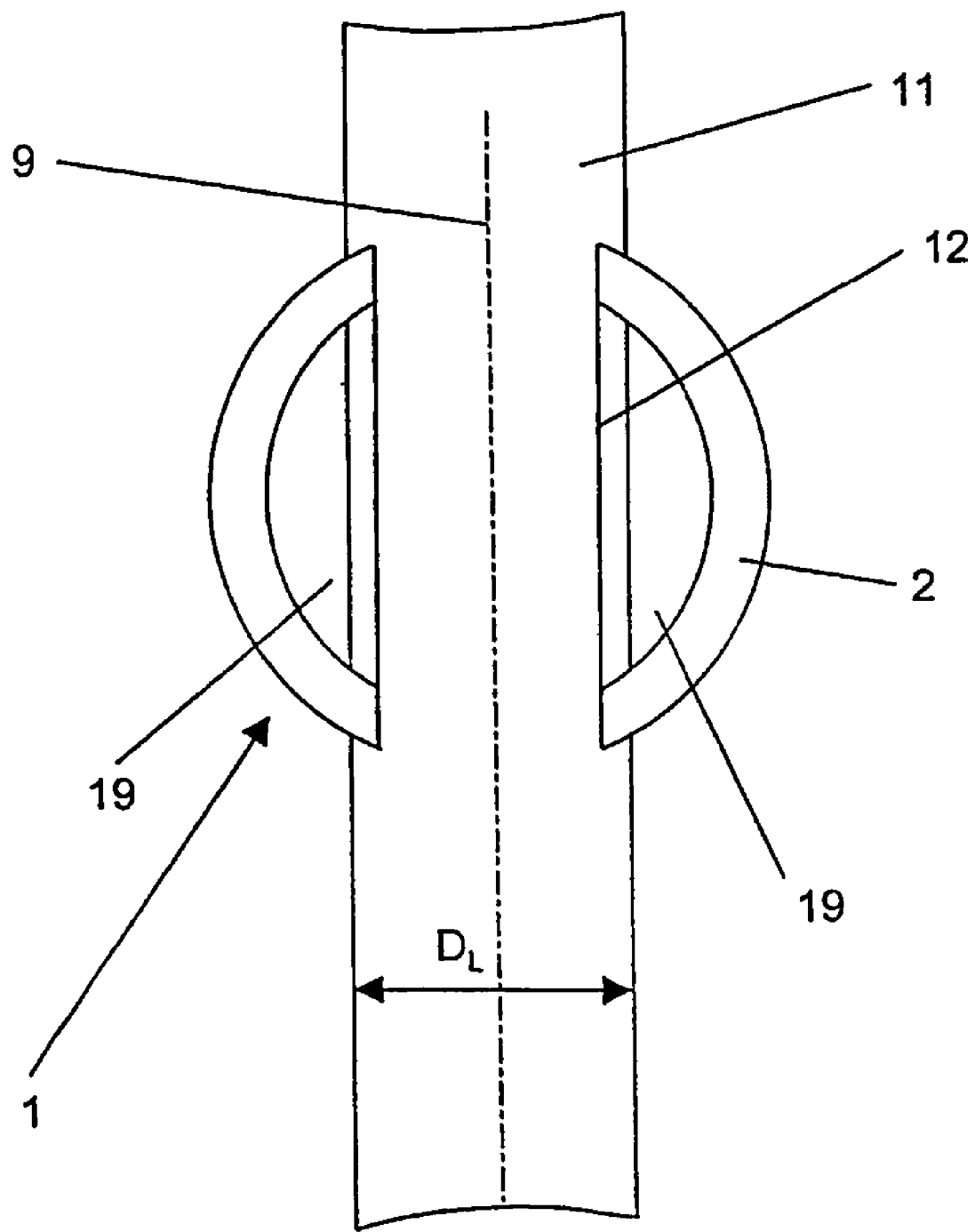
FIG. 3 shows a plan view of the embodiment of the inventive device, shown in FIGS. 1 and 2, with the longitudinal member inserted.
Figure 5:
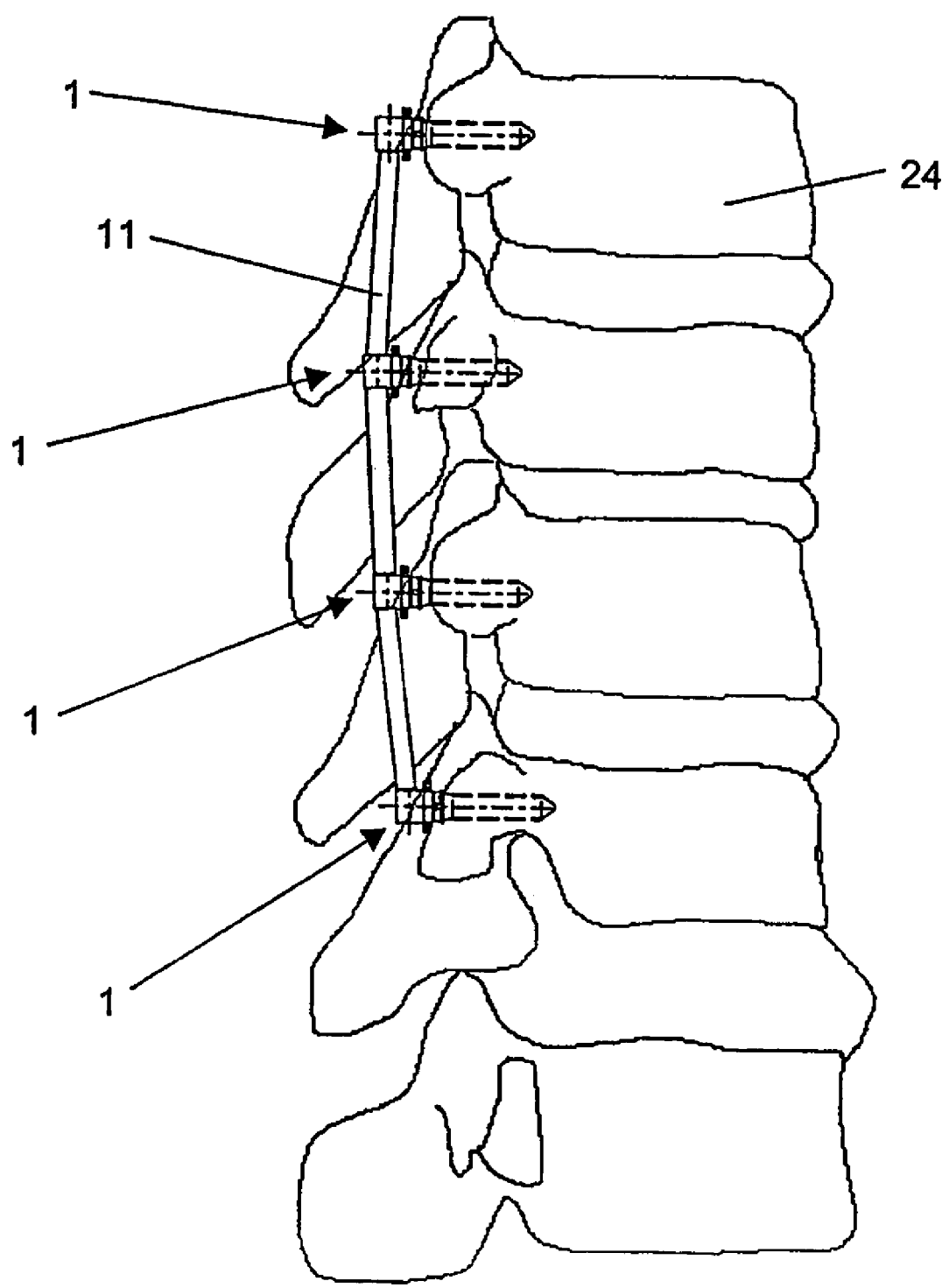
FIG. 5 shows a view of an embodiment of the inventive implant, which is screwed to a part of the spinal column.

FIGS. 1, 2 and 3 generally show a bone fixation means 1 with an upper part 2 and a lower part 3, which are disposed coaxially along a central longitudinal axis 5. The lower part 3, shown as a threaded shaft 4, may be provided with an external thread 6 for securing the bone fixation means 1 into a pedicle of a vertebra body 24 (as best shown in FIG. 5). The upper part 2 is generally in the form of a connecting member for connecting the bone fixation means 1 with a longitudinal member 11, generally shown as a spinal rod. As shown, the upper part 2 generally includes a channel 12, which is sized and configured to receive the longitudinal member 11. The channel 12 passing through the upper part 2 transversely to the central axis 5 and being generally opened at the upper end 13 of the bone fixation means 1.

The upper part 2 may also include a slit 18 generally located between the lower end 14 of the upper part 2 and the channel 12. The slit 18 generally passing through the upper part 2 parallel to the axis 9 of the channel 12 and is open towards the channel 12 thus defining two sidewalls 19 in the upper part 2. As shown, the sidewalls 19 are generally parallel to the central axis 5.

The sidewalls 19, as a result of the slit 18, may be deformed elastically transversely to the axis 9 of the channel 12. That is, as best shown in FIG. 2, the channel 12 generally has an inside width $L_W$ and a reduced width at the upper end 13 of the bone fixation means 1. That is, the channel 12 generally includes a pair of ribs 20 formed at the upper end 13 of the sidewalls 19 to transversely constrict the channel 12 so that a longitudinal member 11, placed in the channel 12, is arrested axially against the upper end 13 of the bone fixation means 1 by the ribs 20.

Moreover, during implantation of the longitudinal member 11, as the longitudinal member 11 is moved into the channel 12, the sidewalls 19 are sized and configured to spread elastically, transversely to the central axis 5, as the longitudinal member 11 is pushed past the ribs 20. Thereafter, as soon as the longitudinal member 11 has been pushed completely into the channel 12, the ribs 19 spring back into their undeformed position.

Figure 4:
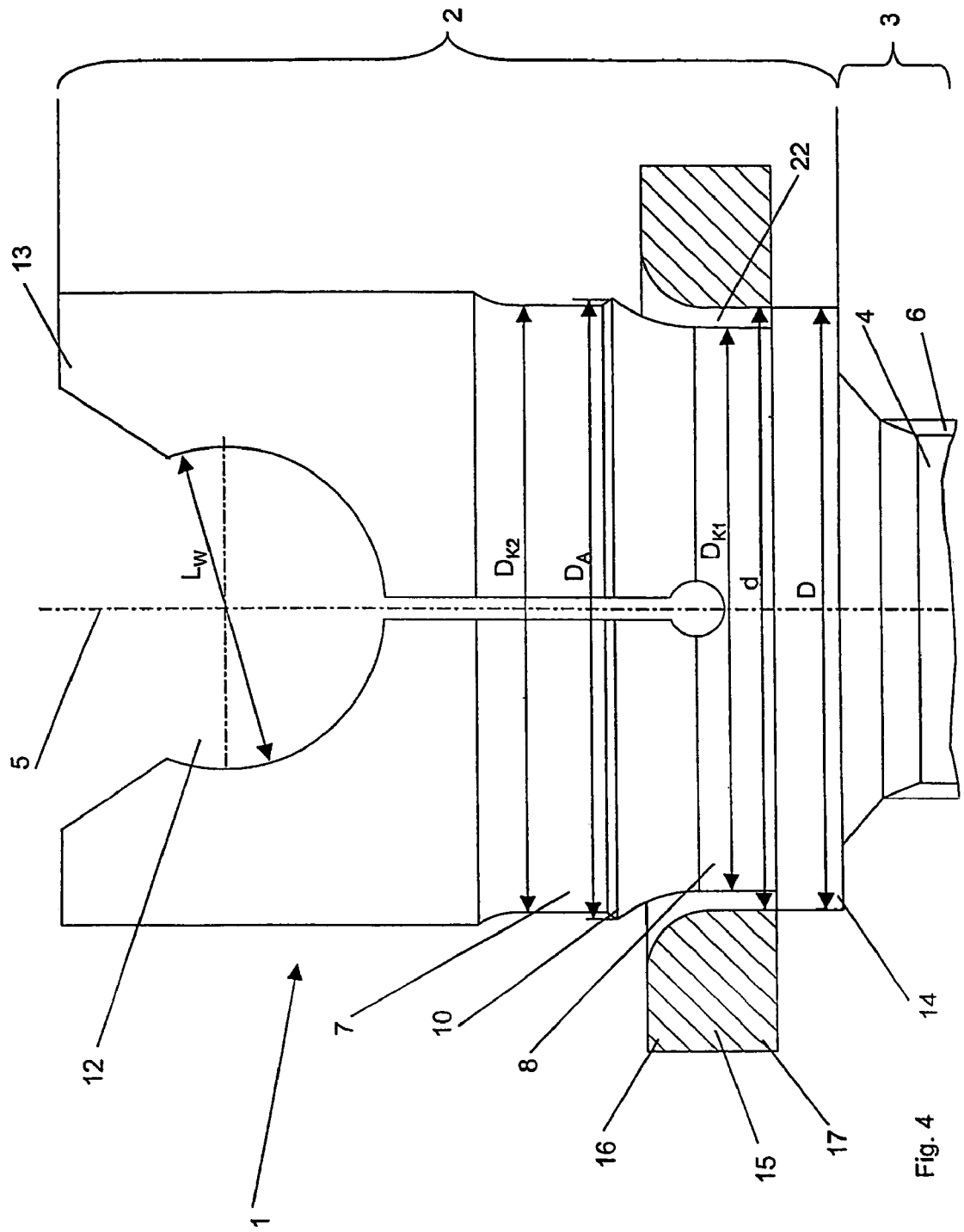
FIG. 4 shows a section of the upper part of an embodiment of the inventive device.

Furthermore, the bone fixation means 1 may also include a first groove 8 formed at the lower end 14 of the upper part 2 and a locking ring 15. The locking ring 15 being moveable from a first position wherein the sidewalls 19 are elastically deformable, as shown in FIG. 2, to a second position wherein the sidewalls 19 are substantially fixed with respect to each other, as shown in FIG. 1. That is, during implantation of the longitudinal member 11 into the channel 12, the locking ring 15 is pushed axially over and aligned with the first groove 8, as shown in FIG. 2. As best shown in FIG. 4, the first groove 8 has a core diameter $D_{K1}$ which is smaller than the diameter d of the central borehole 22 formed in the locking ring 15. This enables the sidewalls 19 to be spread transversely to the central axis 5 without removing the locking ring 15 from the upper part 2 when the locking ring 15 is placed over the first groove 8. Thus, placing the locking ring 15 over the first groove 8 enables the sidewalls 19 to be spread elastically apart with respect to each other so that the longitudinal member 11 can be moved past the ribs 20 and into the channel 12. After the longitudinal member 11 is introduced into the channel 12, the locking ring 15 may be shifted axially into alignment with a second groove 7 formed in the lower end 14 of the upper part 2, which has a core diameter $D_{K2}$ which is larger than diameter $D_{K1}$ so that the sidewalls 19 can no longer be spread elastically apart, such that the longitudinal member 11 can no longer be moved past the ribs 20 thus fixing the position of the longitudinal member 11 inside the channel 12.

More specifically, as shown in FIG. 4, one embodiment of the upper part 2 may include a locking ring 15, a first groove 8, and a second groove 7. The locking ring 15 generally includes a central borehole 22 with a diameter d. The first groove 8 generally has a core diameter $D_{K1}$ which is less than the diameter d of the central borehole 22 formed in the locking ring 15. The second groove 7 generally has a core diameter $D_{K2}$ which is substantially equal to or greater than the diameter d of the central borehole 22 formed in the locking ring 15. So that, during implantation of the longitudinal member 11 into the channel 12 and during the resetting of the bone, which is to be stabilized, the locking ring 15 is pushed over and aligned with the first groove 8 thus enabling the sidewalls 19 to be elastically spread apart so that the longitudinal member 11 may be moved past the ribs 20 formed on the sidewalls 19. Once the longitudinal member 11 is positioned within the channel 12, the locking ring 15 may be moved over and aligned with the second groove 7 by axially shifting the locking ring 15 towards the upper end 13 of the upper part 2. Once the locking ring 15 is moved over and aligned with the second groove 7, the sidewalls 19 can no longer elastically spread apart a sufficient distance such that the longitudinal member 11 can move past the ribs 20. Thus the longitudinal member 11 is fixed inside the channel 15.

As shown in FIG. 4, on the one hand, the core diameter $D_{K2}$ of the second groove 7 is smaller than the diameter of the upper part 2 between the second groove 7 and the channel 12, on the other hand, the upper part 2 may also include a circular shoulder 10 disposed between the first groove 8 and the second groove 7, which has a diameter $D_A$ which is larger than the diameter d of the center borehole 22 formed in the locking ring 15, so that the locking ring 15 may be axially fixed in the second position.

Furthermore, as shown in FIG. 4, the lower end 14 of the upper part 2 may have a diameter D, which is sized and configured so that the locking ring 15 may be brought from the lower part 3 of the bone fixation means 1 into engagement with the first groove 8 during preassembly of the device. However, the locking ring 15 is secured against being shifted inadvertently from the first groove 8 towards the lower part 3 of the bone fixation means 1, by a sharp edge formed at the transition between the first groove 8 and the lower end 14 of the upper part 2. The outlet of the central borehole 22 formed in the locking ring 15 may also be constructed with a sharp edge, so that any inadvertent shifting of the locking ring 15 from the first groove 8 towards the lower end 14 of the upper part 2 is additionally hindered by the two sharp edges.

Shifting the locking ring 15 from the first groove 8 to the second groove 7 may be promoted by a spherical expansion of the central borehole 22 at the upper end 16 of the locking ring 15, as well as by a curved transition formed between the first groove 8 and the shoulder 10.

FIG. 5 shows the inventive implant fastened to a vertebra 24 and a longitudinal member 11.

What is claimed:

1. A device for connecting a longitudinal member to a bone or bone fragment, the device comprising:

an integral bone fixation means having a longitudinal axis, a coaxially disposed lower part for fixation to the bone, and a coaxially disposed upper part having an upper end and a lower end; wherein the upper part includes a channel having an opening at the upper end of the upper part for accommodating the longitudinal member, and a channel axis extending transverse to the longitudinal axis; the upper part further including, between the lower end of the upper part and the channel, a slit which extends parallel to the longitudinal axis and which passes radially through the upper part forming two elastically deformable sidewalls; and a locking ring having a central borehole having a diameter d, the locking ring being moveable from a first position, wherein the two sidewalls are elastically displaceable with respect to the longitudinal axis, to a second position, wherein the two sidewalls are pressed against the channel axis so that the longitudinal member placed within the channel is locked within the channel, the upper part, between the lower end of the upper part and the channel further comprises a first groove, which is concentric with the longitudinal axis and has a diameter $D_{K1}$, wherein the diameter $D_{K1}$ of the first groove is smaller than the diameter d of the central borehole formed in the locking ring so that the locking ring permits the two sidewalls to be elastically displaceable with respect to the longitudinal axis when in the first position;

wherein the upper part further comprises a second groove located between the first groove and the channel, the second groove being concentric with the longitudinal axis and having a diameter $D_{K2}$, wherein the diameter $D_{K2}$ is greater than or equal to the diameter d of the central borehole formed in the locking ring so that the locking ring substantially prevents displacement of the two sidewalls with respect to the longitudinal axis when in the second position; and wherein the upper part, between the first groove and the second groove, further comprises a shoulder, concentric with the longitudinal axis, and having an external diameter $D_A$, wherein the diameter $D_A$ of the shoulder is greater than the diameter d of the central borehole formed in the locking ring and wherein the diameter $D_A$ of the shoulder is greater than the diameter $D_{K1}$ of the first groove and the diameter $D_{K2}$ of the second groove.

2. The device of claim 1, wherein the lower end of the upper part has a diameter D, wherein the diameter D is greater than or equal to the diameter d of the central borehole formed in the locking ring.

3. The device of claim 1, wherein the ratio of the diameter $D_{K2}$ of the second groove to the diameter d of the central borehole formed in the locking ring is between 102% and about 100%.

4. The device of claim 3, characterized in that the ratio of the diameter $D_{K2}$ of the second groove to the diameter d of the central borehole formed in the locking ring is between 100.5% and about 100%.

5. The device of claim 1, wherein the locking ring includes an upper end, the central borehole formed in the locking ring expands spherically towards the upper end.

6. The device of claim 5, wherein the locking ring further includes a lower end, the central borehole formed in the locking ring ending with a sharp edge in the lower end of the locking ring.

7. The device of claim 1, wherein the longitudinal member has a diameter $D_L$; the channel has an interior width $L_W$ in the first position; and the ratio of $L_W$ to $D_L$ is between 90% and 110%.

8. The implant of claim 7, wherein the ratio of $L_W$ to $D_L$ is between 98% and 102%.

9. A device for connecting a longitudinal member to a bone or bone fragment, the device comprising:
   a bone fixation means having a longitudinal axis wherein the bone fixation means comprises a lower part for fixation to the bone and a coaxially disposed upper part having an upper end and a lower end; the upper part including a channel sized and configured to receive the longitudinal member, the channel having a channel axis which extends substantially transverse to the longitudinal axis; the upper part further including a slit between the lower end of the upper part and the channel, the slit defining at least two elastically displaceable sidewalls in the upper end; and
   a locking ring having a central borehole having a diameter d, the locking ring being moveable from a first position, wherein the sidewalls are elastically displaceable with respect to the longitudinal axis so that the longitudinal member can be moved into the channel, to a second position, wherein the sidewalls are substantially fixed with respect to each other so that the longitudinal member placed within the channel is fixed within the channel;
   wherein the lower end of the upper part further comprises a first groove and a second groove, the first and second grooves separated by a shoulder, the locking ring being received within the first groove when in the first position and the locking ring being received within the second groove when in the second position.

10. The device of claim 9, wherein the first groove has a diameter $D_{K1}$, the diameter $D_{K1}$ being smaller than the diameter d of the central borehole formed in the locking ring.

11. The device of claim 10, wherein the second groove has a diameter $D_{K2}$ which is larger than or equal to the diameter d of the central borehole formed in the locking ring.

12. The device of claim 11, wherein the shoulder has a diameter $D_A$ which is larger than the diameter $D_{K1}$ of the first groove and the diameter $D_{K2}$ of the second groove.

13. The device of claim 12, wherein the diameter of the shoulder $D_A$ is larger than the diameter d of the central borehole formed in the locking ring.

14. The device of claim 13, wherein a portion of the upper part located between the first groove and the lower end has a diameter D, which is larger than or equal to the diameter d of the central borehole formed in the locking ring.

15. The device of claim 9, wherein the second groove has a diameter $D_{K2}$ which is larger than or equal to the diameter d of the central borehole formed in the locking ring.

16. The device of claim 15, wherein the ratio of diameter $D_{K2}$ and diameter d is between 102% and 100%.

17. The device of claim 16, wherein the ratio of diameter $D_{K2}$ and diameter d is between 100.5% and 100%.

18. The device of claim 9, wherein the shoulder has a diameter $D_A$, the diameter $D_A$ being greater than the diameter d of the central borehole formed in the locking ring.

19. The device of claim 9, wherein the shoulder has a diameter $D_A$, the ratio of diameter $D_A$ and diameter d is between 101% and 110%.

20. The device of claim 19, wherein the ratio of diameter $D_A$ and diameter d is between 101% and 102%.

21. The device of claim 9, wherein the first groove has a diameter $D_{K1}$, the second groove has a diameter $D_{K2}$, and the shoulder has a diameter $D_A$ the diameter of the shoulder $D_A$ is larger than the diameter $D_{K1}$ of the first groove and the diameter $D_{K2}$ of the second groove.

22. The device of claim 9, wherein a portion of the upper part located between the first groove and the lower end has a diameter D, which is larger than or equal to the diameter d of the central borehole formed in the locking ring.

23. The device of claim 22, wherein the ratio of diameter D and diameter d is between 102% and 100%.

24. The device of claim 23, wherein the ratio of diameter D and diameter d is between 100.5% and 100%.

25. The device of claim 9, wherein the longitudinal member is a spinal rod having an external diameter $D_L$ and the channel formed in the upper part has an inside width $L_w$, the ratio of $L_W$ to $D_L$ being between 98% to 102%.

26. The device of claim 25, wherein the sidewalls each include at least one rib to transversely reduce the width of the channel.

27. The device of claim 26, wherein, in the first position, the sidewalls are sized and configured to elastically spread apart as the spinal rod is moved past the ribs formed on the sidewalls.

28. The device of claim 27, wherein, in the first position, the sidewalls are sized and configured to elastically spread closer together after the spinal rod is moved past the ribs formed on the sidewalls and into the channel.

29. The device of claim 9, wherein the slit is disposed parallel to the longitudinal axis of the bone fixation means.

30. The device of claim 9, wherein the central borehole formed in the locking ring further includes an upper end, a lower end, and a conical expansion at the upper end of the central borehole and with a sharp edge at the lower end of the central borehole.

* * * * *